US006974532B2

(12) United States Patent
LeGeros et al.

(10) Patent No.: US 6,974,532 B2
(45) Date of Patent: Dec. 13, 2005

(54) METHOD FOR PRODUCING ADHERENT COATINGS OF CALCIUM PHOSPHATE PHASES ON TITANIUM AND TITANIUM ALLOY SUBSTRATES BY ELECTROCHEMICAL DEPOSITION

(75) Inventors: Racquel Z. LeGeros, New York, NY (US); John P. LeGeros, New York, NY (US); Shujie Lin, Edison, NJ (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/836,816

(22) Filed: Apr. 30, 2004

(65) Prior Publication Data
US 2005/0000819 A1    Jan. 6, 2005

Related U.S. Application Data

(60) Provisional application No. 60/467,247, filed on May 1, 2003.

(51) Int. Cl.$^7$ .............................. C25D 5/18; C25D 9/06
(52) U.S. Cl. ...................... 205/108; 205/316; 205/322; 205/333
(58) Field of Search ................................ 205/107, 108, 205/318, 333, 316, 322

(56) References Cited

U.S. PATENT DOCUMENTS

| 5,338,433 | A | * | 8/1994 | Maybee et al. ............. 205/178 |
| 5,723,038 | A | * | 3/1998 | Scharnweber et al. ...... 205/107 |
| 5,759,376 | A | * | 6/1998 | Teller et al. ................... 205/50 |
| 6,207,218 | B1 | * | 3/2001 | Layrolle et al. ........... 427/2.27 |

\* cited by examiner

Primary Examiner—Roy King
Assistant Examiner—William T. Leader
(74) Attorney, Agent, or Firm—Klauber & Jackson

(57) ABSTRACT

A method for forming a highly adherent coating of a desired calcium phosphate phase on titanium-based substrates for use as orthopedic and dental implants. The calcium phosphate phase coating is electrochemically deposited onto the substrate from a metastable calcium phosphate electrolyte solution using a modulated electrical potential under pH, temperature and electrolyte composition and concentration conditions favorable for forming the desired calcium phosphate.

8 Claims, 4 Drawing Sheets

SEM of coatings deposited using electrochemical method:.
(A) carbonate-substituted apatite, CHA; (B) calcium-deficient apatite, AP;
(C) fluoride-substituted apatite, FAP; (D) octacalcium phosphate, OCP.

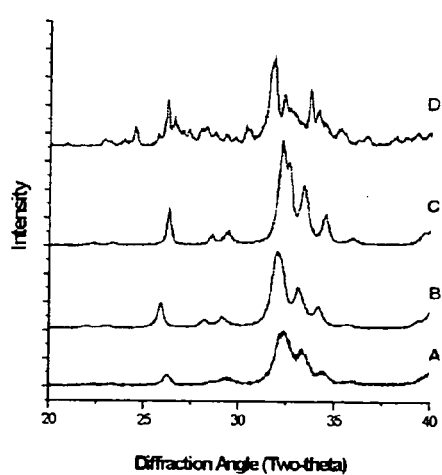

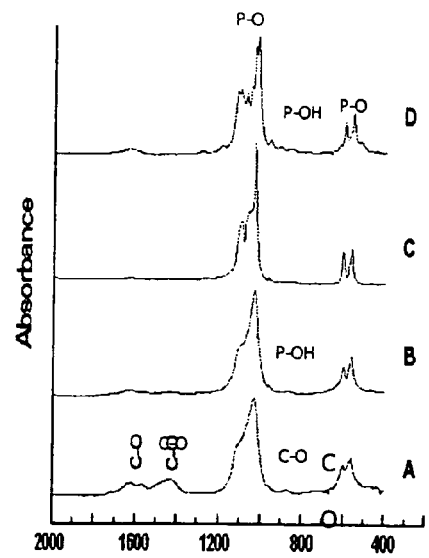

Fig. 1: XRD patterns of coatings deposited using electrochemical method:
(A) carbonate- substituted apatite, CHA;
(B) calcium-deficient apatite, AP;
(C) fluoride-substituted apatite, FAP;
(D) octacalcium phosphate, OCP.
(corresponding FT-IR spectra are shown in Fig. 2)

Fig. 2: FT-IR spectra of coatings deposited using electrochemical method.
(A) carbonate-substituted apatite, CHA;
(B) calcium-deficient apatite, AP;
(C) fluoride-substituted apatite, FAP;
(D) octacalcium phosphate, OCP.

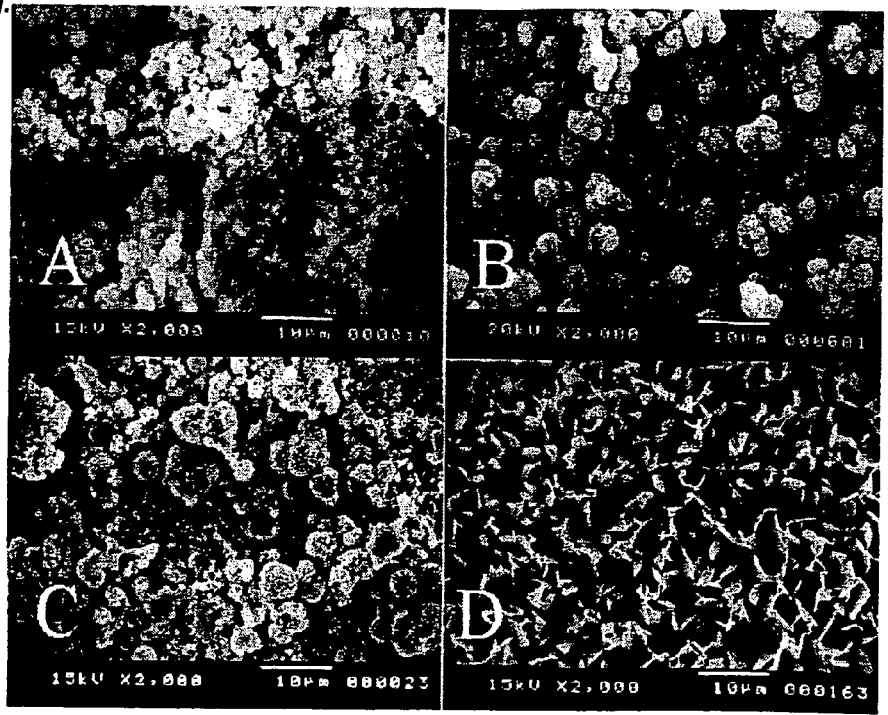

Fig. 3: SEM of coatings deposited using electrochemical method:.
(A) carbonate-substituted apatite, CHA; (B) calcium-deficient apatite, AP;
(C) fluoride-substituted apatite, FAP; (D) octacalcium phosphate, OCP.

METHOD FOR PRODUCING ADHERENT COATINGS OF CALCIUM PHOSPHATE PHASES ON TITANIUM AND TITANIUM ALLOY SUBSTRATES BY ELECTROCHEMICAL DEPOSITION

RELATED APPLICATION

This application claims priority from U.S. Provisional Patent Application Ser. No. 60/467,247, filed May 1, 2003.

FIELD OF THE INVENTION

This invention relates generally to calcium phosphate materials for use in dental and orthopedic applications and more specifically relates to an electrochemical method for depositing coatings of calcium phosphate phases on titanium or titanium alloy substrates.

BACKGROUND OF THE INVENTION

Calcium phosphate (Ca—P) materials commercially available as bone graft or bone substitute materials for dental and orthopedic applications include calcium phosphate phases such as: hydroxyapatite (HA), $Ca_{10}(PO_4)_6(OH)_2$; beta-tricalcium phosphate ($\beta$-TCP), $Ca_3(PO_4)_2$; biphasic calcium phosphate (BCP) consisting of mixtures of HA and $\beta$-TCP; unsintered apatite or calcium-deficient apatite (CDA); coralline HA, and bovine bone derived apatite (sintered and unsintered). These materials are characterized as bioactive, osteoconductive, and promote direct attachment with bone without intervening fibrous tissues, thus developing a very strong interface between the Ca—P material and bone. However, a serious shortcoming of Ca—P materials is their low mechanical or fracture strength and they therefore cannot be used in load-bearing areas.

Commercially pure titanium (cp-Ti) and titanium (Ti) alloy (Ti6Al4V) are metals possessing corrosion resistance, biocompatibility, durability, and strength. These metals are preferred for dental and orthopedic implants or prosthesis. However, these metals do not directly bond to the bone. 'HA-coated' dental and orthopedic implants were therefore developed to combine the bioactivity and osteoconductivity of the 'HA' coating and the properties (e.g., strength) of the Ti or Ti alloy substrate. Plasma spraying is the coating deposition technique used for the commercial 'HA-coated' orthopedic and dental implants. This technique uses HA as the coating source and involves extremely high temperature. The high temperature and other operating parameters produce coatings of variable composition, principally in the ratio of the crystalline (principally HA) to non-crystalline (amorphous calcium phosphate, ACP) phases (HA/ACP ratio). This ratio was found to vary from 30HA/70ACP to 70HA/30ACP in coatings of commercial implants. Of the crystalline phase, 90 to 95% is HA and 5 to 10% is made up of mixtures of tricalcium phosphates ($\alpha$-TCP, $\beta$-TCP), tetracalcium phosphate (TTCP), and sometimes, calcium oxide, CaO. The coating composition (mainly the HA/ACP ratio) significantly affects in vitro dissolution properties of the coating: the lower the ratio, the more soluble the coating. The variability in coating degradation may affect biological performance, coating stability and implant stability. It is therefore necessary to develop alternative coating methods using low temperature that will provide coatings with reproducible homogeneous composition.

Deposition of brushite or dicalcium phosphate dihydrate (DCPD), $CaHPO_4 \cdot 2H_2O$, dicalcium phosphate anhydrous (DCPA) or monetite, $CaHPO_4$, and apatite (AP) has been achieved using electrochemical deposition method AP coatings have also been obtained by transformation of the initially formed DCPD or DCPA coating. In studies relating to these, neither the adherence of the ECD-deposited calcium phosphate coating to the substrate nor the dissolution properties of the coatings was reported.

Octacalciumphosphate (OCP), $Ca_8H_2(PO_4)_6 \cdot 5H_2O$, one of the biologically relevant calcium phosphates, can easily transform to carbonate hydroxyapatite (CHA) in synthetic systems. Because of structural similarity between OCP and HA, $Ca_{10}(PO_4)_6(OH)_2$, OCP is speculated to be a necessary precursor of bone apatite which is a carbonate hydroxyapatite (CHA). OCP has been demonstrated to be more resorbable and to enhance more bone formation than either HA or $\beta$-TCP.

SUMMARY OF THE INVENTION

Now in accordance with the present invention, an electrochemical method is provided for depositing adherent octacalciumphosphate (OCP) and other coatings of calcium phosphate phases on commercially pure titanium or titanium alloy (e.g. Ti6Al4V) substrates of different shapes and different surface preparations. Calcium phosphate phases that can be electrochemically deposited include: amorphous calcium phosphate, ACP (of different compositions—including incorporation of Zn, Mg, F, $P_2O_7$, organic moieties, etc); dicalcium phosphate dihydrate, DCPD, $CaHPO_4 \cdot 2H_2O$; dicalcium phosphate anhydrous, DCPA, $CaHPO_4$; octacalcium phosphate, OCP, $Ca_8H_2(PO_4)_6 \cdot 5H_2O$; substituted tricalcium phosphate, $\beta$-TCP (substituted with Mg, Zn, etc); calcium-deficient apatite, HAp (of different calcium deficiency); biphasic calcium phosphate, BCP, consisting of mixture of HAp and substituted $\beta$-TCP of varying HAp/$\beta$-TCP ratios; substituted apatites: carbonate hydroxyapatite, CHA; fluoroapatite, FA, carbonate and F-substituted apatites, CFA; chloro-apatite, ClAp or (Cl,OH)-Ap; Strontium apatite, SrAP or (Sr,Ca)AP. In addition other substituents may also be deposited (e.g., borate, manganate, citrate, etc.)

In addition, originally deposited calcium phosphate phase can be transformed to other calcium phosphate phases (e.g. ACP to DCPD or HAp or substituted HAp; DCPD or DCPA to substituted HAp or substituted $\beta$-TCP; OCP→substituted HAp; etc). Bioactive molecules or drugs can be incorporated in the electrochemically deposited calcium phosphate—allowing their controlled release or delivery in vivo.

Titanium (Ti) alloy plates, tensile bars with various types of surfaces (e.g., grit blasted with apatitic abrasive, chemically textured, arc-deposited, and CoCr-beaded) and dissolution cylinders are electrochemically coated using modulated pulse time electric fields which can be programmed by a microprocessor. Modulated electrochemical deposition (MECD) is carried out using pH and temperature conditions favorable for OCP or other calcium phase formation. Coatings produced by the invention were characterized using x-ray diffraction, FTIR, scanning electron microscopy, tensile strength tests and solubility tests. XRD and FTIR analyses showed that pure uniform OCP coatings were produced on Ti6Al4V surfaces with coating to substrate tensile strengths greater than 7000 psi. Coatings on Ti Arc-deposited surfaces, chemically textured surfaces and CoCr beaded surfaces all gave tensile strengths ranging from 5000 psi to 7000 psi with no coating shadows in the crevices. Dissolution of OCP coating in 100 ml of 0.1M Tris Buffer solution was determined from the amount of calcium (Ca) released onto the buffer which was 7.7±1.0 ppm Ca at pH 7.3 after 4 hr, and 22±1.4 ppm Ca at pH 3 after 2 hr. OCP crystal size can be controlled by the current density and relative pulse time modulation. Thus, by use of the invention: (1) highly adherent calcium phosphate (e.g., OCP) coating of uniform compositions (e.g., OCP) on Ti alloy substrates can be obtained at low temperatures using MECD by optimizing pulse time modulation of the electric field, reaction pH, temperature and electrolyte composition; and (2) OCP readily transforms to CHA when exposed to SBF.

BRIEF DESCRIPTION OF DRAWINGS

In the drawings appended hereto:

FIG. 1 is a graph depicting XRD patterns of several calcium phosphate phase coatings deposited by the method of the invention;

FIG. 2 is a graph depicting FT-IR patterns of several calcium phosphate coatings deposited by the method of the invention;

FIG. 3 is a series of SEMs of different calcium phosphate phase coatings deposited by the method of the invention.

DESCRIPTION OF PREFERRED EMBODIMENTS

Sample Preparation

Figure 4:
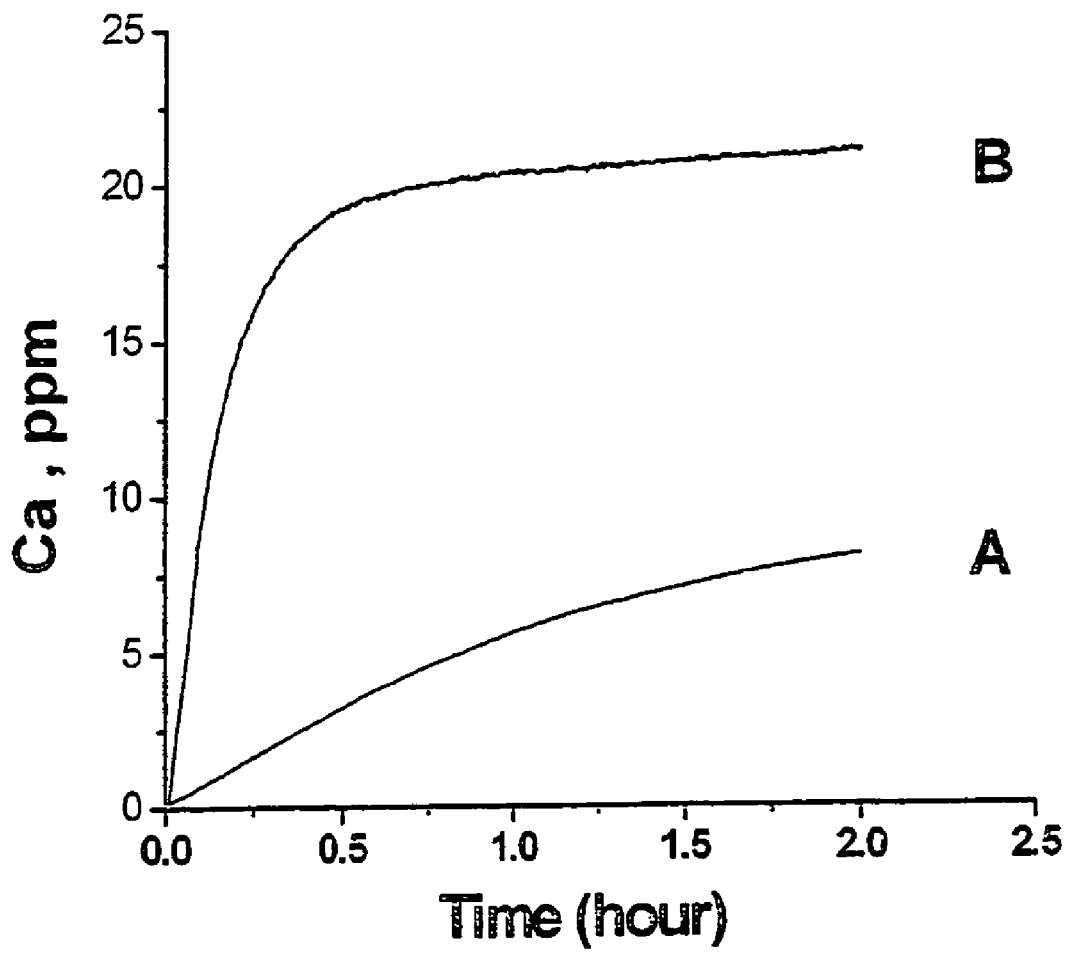
FIG. 4 is a graph depicting dissolution of an electrode-posited OCP coating under several conditions.

Three (3) types of Ti alloy (Ti6Al4V) substrates and Ti alloy bars with four (4) different surface preparations were used to demonstrate the invention. The three types were: plain Ti alloy plate, 25×25×1.5 mm$^3$, tensile strength bars, diameter, 25 mm, length 42 mm and dissolution cylinders, diameter, 12 mm, length 25 mm. The four kinds of surface preparations were: grit blasted with an apatitic abrasive (MCD abrasive, HiMed, Bethpage); arc-deposited; chemically textured and coated with Co—Cr beads. The plates and dissolution cylinders were grit blasted with apatitic abrasive. The arc-deposited, chemically textured and Co—Cr beaded surfaces were received from Stryker-Howmedica-Osteonics. Arc-deposited means that the Ti coating was deposited by melting Ti wire with an electric arc (high voltage/high current) onto the surface. Chemical treatment was by acid-etching. Co—Cr beaded surfaces were obtained by bonding Co—Cr beads (425–500 microns in diameter) onto a Co—Cr substrate. Twelve (12) samples of each type of surface (grit-blasted with apatitic abrasive, arc-deposited, and coated with Co—Cr beads) and six (6) samples of chemically textured surfaces were coated with OCP for tensile-strength measurements. Twelve (12) grit-blasted OCP-coated cylinders were used for dissolution studies, using six (6) cylinders for each pH (pH 3.0 and pH 7.4). The coating on plates were used for analyses using scanning electron microscopy (SEM), x-ray diffraction (XRD), Fourier transform infrared (FTIR) spectroscopy and inductive coupled plasma (ICP) for elemental analyses and for transformation experiments in simulated body fluid (SBF). Coated tensile bars were used for tensile measurements.

All substrates were cleaned ultrasonically, acid etched for 30 minutes, rinsed and dried. Nail vanish was applied on the substrates except for a circular area (diameter, 1.0 cm) at the center. Two similar substrates were used as anode and cathode; the separation distance was kept constant. MECD was carried out using modulated pulse time electric fields programmed with a custom-made dual microprocessor. The pH and temperature conditions for OCP formation were according to methods previously described (LeGeros, R. Z., et al. (1989) Scan Electron Micro. 3:129–138, LeGeros R. Z., et al. (1991) Monographs in Oral Sciences 15:, LeGeros, R. Z., et al. (1984) Scan Electron Micros 4:1771–1777 and LeGeros, R. Z. (1985) Calcif Tissue Int. 37:194–197). Metastable calcium phosphate solutions for coating were prepared by mixing 100 ml 0.01M Ca(Ac)$_2$ and 100 ml 0.0067M NaH$_2$PO$_4$ solutions.

(Metastable calcium phosphate solutions can be used at different pH and temperature conditions and electrolyte concentration to obtain the desired calcium phosphate). See R. Z. LeGeros, 1991, *Calcium Phosphates in Oral Biology and Medicine*. Monographs in Oral Sciences. Vol. 15, H. Meyers, ed; Karger, Basel). The electrochemical deposition solution can be at temperatures from room temperature to about 95° C. The present pH used depend on the desired calcium phosphate phase and generally will be in the range of 4 to 12. The solution composition depends on the calcium phosphate phase desired or desired substitution in the HAp or b-TCP.

As set forth in such reference, the types of Ca—P formed are dependent on the following solution conditions: pH, temperature, ionic concentrations, Ca/P molar ratio, and presence of inorganic or organic elements. Other factors such as rate of stirring or digestion time also exert an influence. Amorphous Calcium Phosphate, ACP is obtained only under conditions of high supersaturation, high pH, at room temperature, from solutions containing only calcium and phosphorous ions. ACP does not form under conditions of low supersaturation or of high supersaturation when the initial solution pH is lower than 9. ACP can be obtained at lower pH (even at pH 6) and even at higher temperature (60 or 95° C.) when other elements such as $Mg^{2+}$, $Sn^{2+}$, $Al^{3+}$, $P_2O_7^{4-}$, or $CO_3^{2-}$ are simultaneously present with the $Ca^{2+}$, $PO_4^{3-}$ and $HPO_4^{2-}$ ions in solutions.

Dicalcium Phosphate Dihydrate Brushite, CaHPO$_4$ 2H$_2$O, DCPD formation from solutions is usually favored at low pH (4–6) at 25 or 37° C., at different levels of saturation, or at physiological pH (7 or 7.5) when the total Ca and total inorganic phosphate, Pi ($HPO_4^{2-}+PO_4^{3-}$) expressed as ($Ca^{2+}$) (Pi), exceeds 5 mM/1, DCPD is also obtained under conditions of supersaturation normally favoring the formation of other Ca—P phases when conditions are modified or other elements are present simultaneously with $Ca^{2+}$ or Pi.

Direct formation of OCP octacacalcium phosphate, Ca$_2$H$_2$(PO$_4$)$_6$.5H$_2$O. is favored at 37° C., pH 6.5; 60° C., pH 6; 70° C. pH 5; 80° C., pH 4 at high levels of saturation.

Under conditions normally favorable for the exclusive formation of OCP (e.g., pH 5 or 6, 60° C.), the presence of F$^-$ promotes the formation of (F,OH)-apatite.

Regardless of the systems used, the pH/temperature effect is more dominant than the solution Ca/P ratio in influencing the type of Ca—P phase formed. The pH/temperature effect however is modified by the presence of other ions. For example, magnesium allows the formation of DCPD even at higher pHs where the formation of other Ca—P phases (OCP, AP) are normally favored; promotes the formation of Mg-substituted whitlockite from aqueous systems where pure whitlockite does not form, and promotes the formation of Mg-containing ACP. Fluoride allows the formation of apatite at the expense of CDPD, OCP or Mg-substituted β-TCMP. The LeGeros Monograph cited may be referred to for further details on production of the calcium phosphate phases.

Plating current pulse times, e.g., with square pulses, can generally range from about 200 μsec to 20 sec, and the ON/OFF ratio can be in the range of 10:1 to 1:100. Plating current density is generally in the range of 200 $\mu A/cm^2$ to 3 $ma/cm^2$. Coating thickness can be varied by controlling the deposition time.

The pH of each electrolyte was adjusted to 5.0 with HCl (0.1 M/L) using a combined pH glass electrode at room temperature. After mixing and stirring, the pH of the solution was adjusted again to 5.0 at 60° C. The solution temperature during the process was kept constant in a water-bath maintained at 60° C. MECD deposition was performed under controlled pulse current time and average current density of 4 $ma/cm^2$ for 30 minutes. Preliminary experiments were first performed to determine the effect of varying the nature of the modulation on OCP crystal size. These experiments showed that OCP crystals as large as 5 μm are obtained when using a deposition program giving an "ON" pulse (potential applied) of 20 sec followed by an "OFF" pulse of 40 sec; or OCP crystals smaller then 2 μm, are obtained using a deposition program giving an "ON" pulse of 5 sec followed by an "OFF" pulse of 5 sec. After the coating process, coated samples were washed with distilled and deionized water and air-dried.

Characterization of the OCP Coatings

Coating thickness was measured using a microscopic focusing technique.

The coatings were scraped from some plate substrates and powdered (<90 microns) before FTIR, XRD and ICP analyses.

FTIR analyses were made on a Nicolet 550 Series II. Micro-pellets were prepared by mixing 1.0 mg of the scraped powdered coating with 300 mg KBr (IR grade, Perkin-Elmer, Connecticut) pressed under 10,000 psi.

XRD analyses were made on Philips APD 3520 using curved crystal monochromator and Cu radiation generated at 45 kV and 50 mA and using Arkansas quartz as standard. The scraped powdered coating was placed on a quartz plate to reduce background radiation and improve the signal to noise ratio. For X-ray microcamera, the powdered coating was dispersed as a thin film on a piece of scotch tape. The scotch tape was loaded in microcamera, the dental negative film was exposed for 2 hours and developed.

Scanning electron microscopy (SEM) analyses were made using JEOL 5400 operating at 20 KV. The coated plates were mounted on aluminum holder and coated with platinum.

For analyses of calcium and phosphate ion concentrations of the coating, ICP analyses were made on Thermal-Electron Incorporated apparatus (Franklin, Mass.). 1 mg of powdered coating was dissolved using a few drops of 17% HCl and diluted to 25 ml in a volumetric flask using an acidic mixture solution (5% HCl and 2% $HNO_3$). Standard calcium and phosphate solutions were prepared by diluting standard calcium and phosphate solutions (Fischer Scientific, New Jersey) with the same acidic mixture solution.

Tensile Bond Strength Determination

The tensile strength measurements were made using the facilities at Stryker-Howmedica-Osteonics laboratories in New Jersey in accordance with ASTM specifications ("Specifications for calcium phosphate coating for implantable materials"). Specimen geometry and test procedures complied with Osteonics Mechanical Test Procedure MTP002 (ASTM F1501) using one layer (0.010 in.) of FM 1000® sheet adhesive (American Cyanamid. Wayne, N.J.) was utilized to bond specimen/grit-blasted mating plug on the coatings. The cure cycle for all specimens was 180° C.±5° for 90 minutes. After cooling, the excess adhesive was removed by lightly melting.

An Instron Model 4505 Universal Testing System under Series IX computer control was employed for testing. The crosshead displacement rate was 0.05 in./min. Gross visual observations and a stereoscope was used to determine the models of failure.

Evaluation of the Dissolution Property of the Coatings

Dissolution studies were made by suspending OCP-coated cylinders in 100 ml of 0.1M Tris buffer solution (37° C.), stirring rate 150 rpm, for 4 hrs at pH 7.3 (n=6) and 2 hrs at pH 3 (n=6). A custom-made water bath accurate to ±0.1° C. was part of the dissolution system. Six (6) of cylinders were immersed in 100 ml of 0.1M Tris buffer solution for each pH (pH 3.0 and pH 7.4), 37° C. for 2 hours. Dissolution experiments performed at pH 3 reflect the acidic pH environment of osteoclast cells while those performed at pH 7.3 reflect the normal physiological pH. The calcium (Ca) ions released from the coating onto the buffer with time was monitored using a Ca-ion selective electrode coupled with Metrohm 692 pH/Ion Meter connected to an IBM PS desktop computer. The dissolution procedure was in accordance with ASTM F1926 specifications ("Test method for evaluation of the environmental stability of calcium phosphate coating").

Transformation of the OCP Coating.

Six (6) coated plates were suspended in simulated body fluid at pH 7.25, 37° C. for one week. SBF solution was prepared according to Kokubo, T., (1996) Thermochim Acta, 280:479–490. Formation of carbonate hydroxyapatite was characterized using FTIR, XRD and SEM.

RESULTS

Composition, Crystallinity, Morphology and Thickness of the Coatings.

The calcium phosphate phase coating was shown by FTIR (FIG. 2 curve D), XRD (FIG. 1,curve D) to consist of only OCP. (The Figures also show the patterns for additional calcium phosphate coatings that can be deposited by the present invention by use of suitable pH and temperature conditions and electrolyte concentration). XRD microcamera film showed a small diffraction ring (100) near the center, the strongest diffraction peak for OCP at 4.8°2θ. ICP analyses showed the Ca/P ratio of 1.33+0.05 further confirming the coating composition (Ca/P of pure OCP=1.33). The coating was shown by SEM to be composed of thin platy crystals (FIG. 3D). The crystal size of OCP was influenced by the parameters of current density, pulse time modulation and pulse time frequency: the lower the current density, the larger the crystal size and the shorter the pulse time frequency, the smaller the crystal size. The average coating thickness on various types of surfaces was 19 microns. The coating thickness on the four kinds of surface was not significantly different (Anova test, p<0.05). Coating thickness can be increased by increasing the time of deposition.

Tensile Strength of OCP Coatings

The coatings on the surface grit-blasted with apatitic abrasive (n=12), chemically textured (n=6), arc-deposited (n=12) and CoCr-beaded-surfaces (n=12), are all different. Tensile strength of the coating on various types of surfaces ranged from 5,000 to 7,000 psi (35 MPa to 52 MPa). The tensile strengths of the coating on these four kinds of surfaces as a group were significantly different from each other (Anova test, p<0.01). The tensile strength on arc-deposited, CoCr-beaded surfaces and chemically textured surfaces were not significantly different from each other (student t-test, p>0.05). The mean tensile strength of the surface grit blasted with apatitic abrasive was found to be significantly higher than those from the arc-deposited, CoCr-beaded and chemically textured surfaces (0.05>p>0.002).

Dissolution Property of the Coatings

The mean calcium concentration (ppm Ca) was 7.7±1 ppm at pH: 7.3 after four hours (A in FIG. 4) and 22±1.4 ppm at pH 3 (B in FIG. 4) after two hours.

Transformation of OCP Coating in SBF

Figure 5:
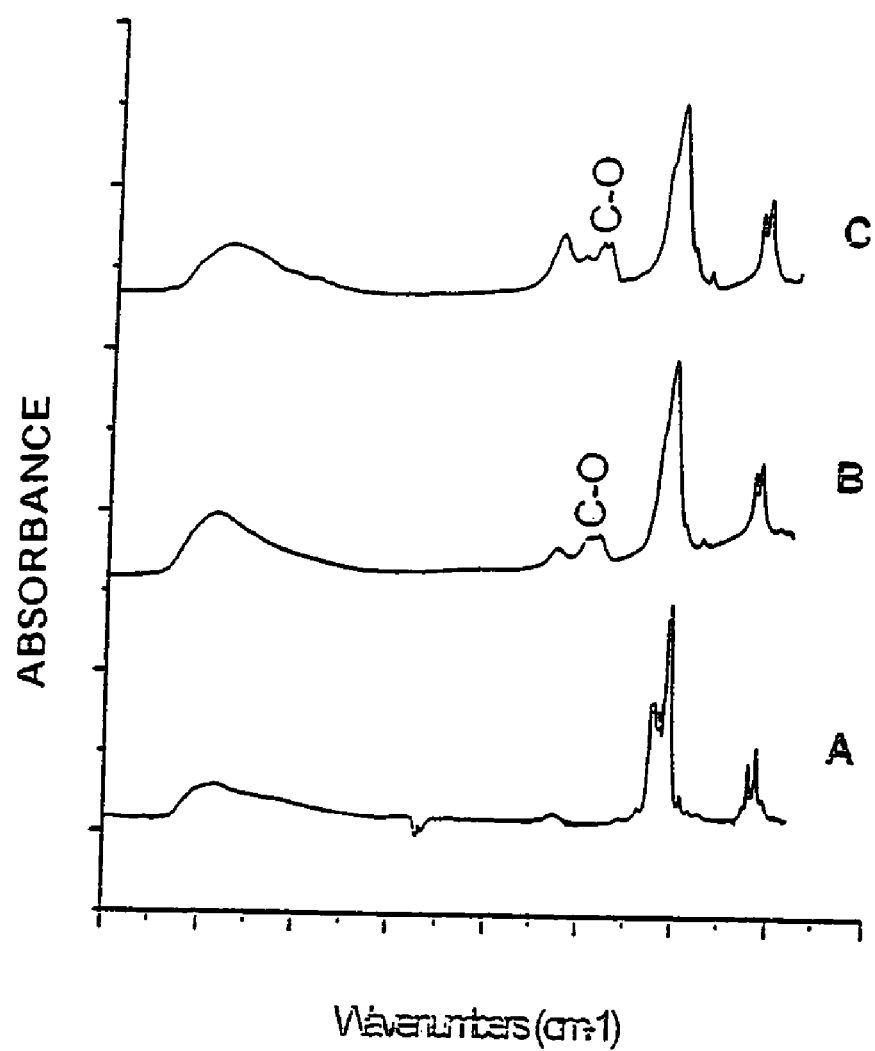
FIG. 5 is an FTIR of an OCP coating before and after transformation to CHA and under several other specified conditions.
Figure 6:
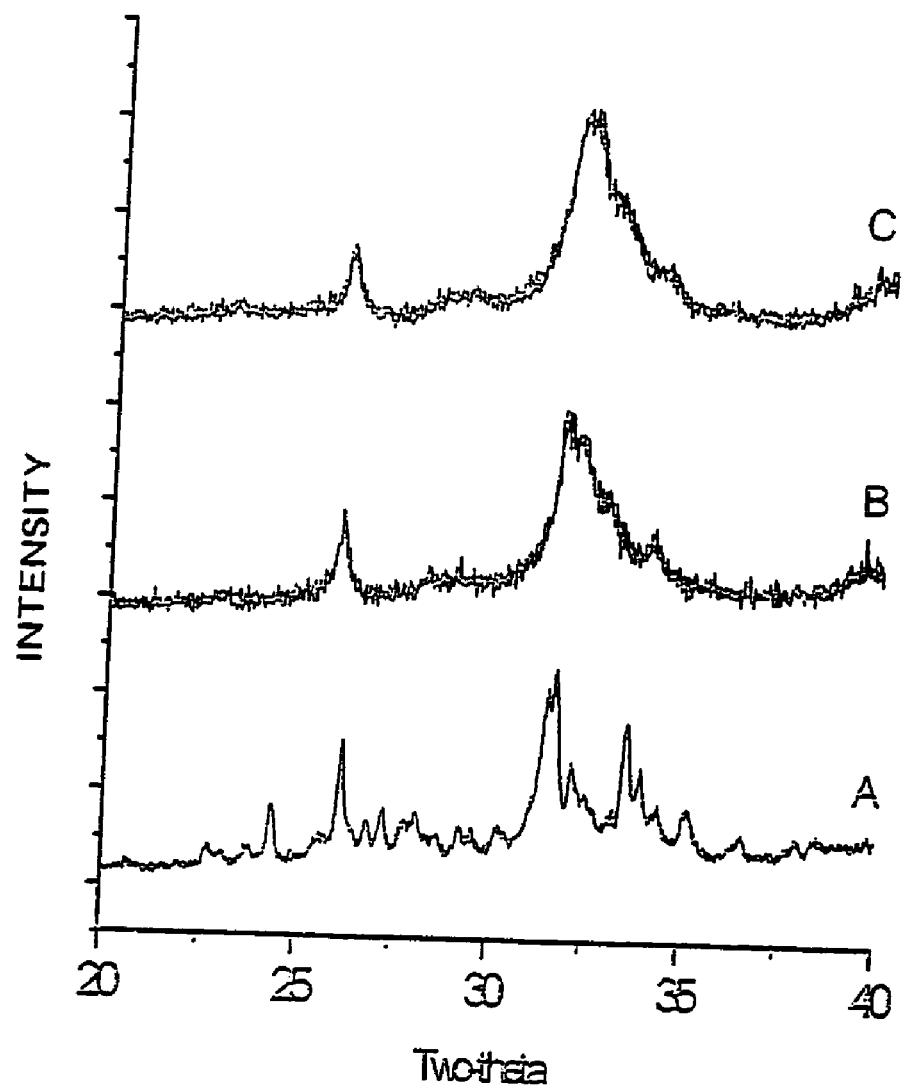
FIG. 6 depicts XRD profiles before and after transformation to CHA.

The OCP coating (Curve A in FIG. 5) was transformed to CHA after immersion in SBF as shown by FTIR (Curve B in FIG. 5. Curve C shows the FTIR spectrum of cowbone for comparison). Crystallinity (reflecting crystal size and/or perfection) is shown by the XRD before and after transformation to CHA profiles (curves A and B in FIG. 6) to be similar to that of cowbone apatite (Curve C in FIG. 6). SEM showed differences in morphology and size of the coating crystals before and after exposure to SBF.

DISCUSSION

Plasma-sprayed HA coating has been shown to enhance bone apposition and interfacial strength compared with uncoated Ti or Ti alloy dental and orthopedic implants. However, the plasma-spray process, being a line-of-sight process, is not suitable for coating porous surfaces and implants of complex geometry. Furthermore, because this process involves very high temperatures, coating composition (principally, HA/ACP ratio) can vary between coating layers (e.g., closest to and farthest from the metal substrate). Because of the preferential dissolution of the ACP component, the variation in the HA/ACP may affect biodegradation and stability of the coating and, ultimately, the stability of the implant.

In use of the modulated electrochemical deposition for Ca—P phases on the Ti alloy, cathodic polarization of Ti alloy leads to an increase in pH at the interface between the alloy and electrolyte due to the formation of $OH^-$ ions. The sudden increase in pH triggers crystal nucleation and initiates crystal growth of the desired calcium phosphate phase directly on the substrate surface. OCP crystal size can be controlled by current density and relative pulse time modulation. Crystals grown at high current density were smaller than those obtained at low current density indicating that more ions had much higher probability of interacting with each other and forming larger number of nuclei sites at high current density. The crystal size was also related to the duration of the pulse current: the longer the duration, the larger the crystal size. Appropriate modulation of pulse current time allows the slower phosphate ions ($H_2PO_4^-$, $HPO_4^{2-}$, $PO_4^{3-}$) to catch up and join faster calcium ions ($Ca^{2+}$) to form Ca—$PO_4$ nuclei that will eventually grow to OCP crystal.

By use of the invention, uniform OCP deposition was made on Ti alloy surfaces regardless of shapes (plates or cylinders) or surface preparation (grit blasted with apatitic abrasive, arc-deposited, chemically treated or Co—Cr beaded). Coatings consisting of desired calcium phosphate phases (e.g., DCPD, DCPA, calcium deficient apatites, (F,OH)-apatite or carbonatehydroxyapatite) can be obtained using the right combination of pH, temperature and solution composition.

Tensile Strength

Prior reported studies on electrodeposition of calcium phosphates (e.g. brushite, monetite, apatite) have not included information on the tensile strength between the coating and the metal substrate. We have found, using an Instron Universal testing system, that by employing the present invention the tensile strengths of the OCP coating on different surfaces ranged from 5000 psi to 7000 psi (35 MPa to 50 MPa). The tensile strength measurements were made on OCP coating before immersion in SBF. The tensile strength value was highest for the OCP coated on surface roughened by grit blasting with apatitic abrasive. Since the microporosities of the OCP coatings on surfaces receiving different treatments were similar, the observed higher tensile strength on surfaces grit blasted with apatitic abrasive cannot be attributed to the possible contribution of the glue used. Instead, it may be due to the difference in surface roughness introduced by the different treatments (grit blasting with alumina, acid treatment, arc deposited Ti or Co—Cr beaded).

Dissolution Properties of OCP Coatings

In vivo studies on calcium phosphate coated (plasma-sprayed 'HA') implants indicated the importance of initial coating properties on the implant fixation and bone apposition. Dalton and Cook (Dalton, J. E. et al. (1995) J Biomed Materials, 29:239–245) have shown that degradation of some HA-coated implants resulted in less bone apposition than stable HA coatings. (Nagano, M. et al. (1996) Biomaterials, 17:1771–1777) found that when an amorphous coating dissolved, bone directly apposed underlying material. Initial studies on in vitro dissolution of plasma-sprayed 'HA' coatings showed that variability in the dissolution properties paralleled the variability in the coating composition, principally the HA/ACP ratio. ASTM testing of properties of plasma-sprayed HA coatings include in vitro dissolution in neutral and acidic solutions. In this study, neutral pH (7.4) represented normal physiological pH and acidic pH (3) represented the pH of the environment during osteoclast-mediated activity on the coatings.

The optimal biodegradation characteristics of calcium phosphate coatings are yet to be resolved. A coating that is too soluble can degrade before enhanced stability is gained from the calcium phosphate activity. Stable coatings, which are not readily resorbed or biodegraded, are not as bioactive as the more degradable coatings. Additionally, the less stable coatings (e.g., plasma-sprayed HA coatings with low HA/ACP ratio) may eventually delaminate and separate from the underlying metallic structure. A coating with some intermediate degradation response may be optimal for implant fixation.

Application of the method of invention showed low variance standard variation in the dissolution data of the ECD deposited OCP coating indicating homogeneous and consistent coating composition. This is a decided advantage compared to the variability in the composition (mainly HA/ACP ratio) of the plasma-sprayed 'HA' coating.

CONCLUSION

Modulated electrochemical deposition (MECD) is an alternative method to plasma-spray technique for coating calcium phosphate on the metal alloy at low temperature. The MECD method consists of depositing calcium phosphate coatings on implant surfaces by immersion in an aqueous electrolyte containing Ca and P ions under modulated controlled potential and current at low temperature (<100° C.). This method has the following advantages over high temperature techniques: (a) provides a more uniform and predictable coating composition onto implants of complex geometry or porosity; (b) does not cause any adverse heat effects on the substrates; (c) co-precipitation of bioactive molecules of growth factors can be made if desired. Highly adherent, calcium phosphate coatings on Ti alloy substrates can be obtained at low temperature using the MECD method by optimizing pulse time modulation of the electric field and using appropriate reaction pH, temperature and electrolyte composition. The MECD deposited OCP coatings show homogenous morphology, composition, thickness and dissolution properties.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

What is claimed is:

1. A method for forming a highly adherent coating of a desired calcium phosphate phase on a titanium-based substrate for use as an orthopedic or dental implant, comprising:

electrochemically depositing the coating of said calcium phosphate phase onto said substrate from a metastable calcium phosphate electrolyte solution using a modulated electrical potential under pH, temperature and electrolyte composition and concentration conditions favorable for forming the desired calcium phosphate phase;

said deposition temperature range being from room temperature to 95° C.;

said pH being in the range of 4 to 12;

said modulated electrical potential providing plating current pulse time based on square pulses being in the range of from about 200 $\mu$sec to 20 sec and the ON/OFF ratio being in the range of 10:1 to 1:100, and plating current density being in the range of 200 $\mu a/cm^2$ to 4 $ma/cm^2$; and wherein said substrate surface prior to said electrochemical deposition is prepared by a surface preparation treatment selected from the group consisting of (1) grit blasting with an apatitic abrasive, (2) arc-deposition of titanium; (3) chemically texturing; and (4) coating with Co—Cr beads.

2. A method in accordance with claim 1, wherein said substrate is an alloy of titanium.

3. A method in accordance with claim 1, wherein said substrate is substantially pure titanium.

4. A method in accordance with claim 1, wherein said calcium phosphate phase comprises octacalcium phosphate.

5. A method in accordance with claim 1, wherein said calcium phosphate phase comprises a carbonate-substituted apatite.

6. A method in accordance with claim 1, wherein said calcium phosphate phase comprises a calcium deficient apatite.

7. A method in accordance with claim 1, wherein said calcium phosphate phase comprises a fluoride-substituted apatite.

8. A method in accordance with claim 1, wherein the crystal size of the calcium phosphate phase deposit is controlled by one or both of the duration of the current pulses and of the plating current density.

* * * * *